US005328896A

United States Patent [19]
Riebel et al.

[11] Patent Number: 5,328,896
[45] Date of Patent: * Jul. 12, 1994

[54] PREPARING HERBICIDAL SULPHONYLUREA SALTS

[75] Inventors: Hans-Jochem Riebel; Christa Fest, both of Wuppertal; Rolf Kirsten, Monheim; Joachim Kluth, Langenfeld; Klaus-Helmut Müller, Düsseldorf; Dieter Feucht, Monheim; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[*] Notice: The portion of the term of this patent subsequent to Oct. 15, 2005 has been disclaimed.

[21] Appl. No.: 46,106

[22] Filed: Apr. 9, 1993

Related U.S. Application Data

[63] Continuation of Ser. No. 852,611, Mar. 17, 1992, abandoned, which is a continuation-in-part of Ser. No. 626,363, Dec. 12, 1990, abandoned.

[30] Foreign Application Priority Data

Dec. 19, 1989 [DE] Fed. Rep. of Germany ....... 3941790
Jun. 8, 1990 [DE] Fed. Rep. of Germany ....... 4018349

[51] Int. Cl.$^5$ .................. A01N 43/66; C07D 251/42
[52] U.S. Cl. .................................... 504/227; 544/208
[58] Field of Search ............... 544/208, 211; 504/227

[56] References Cited

U.S. PATENT DOCUMENTS 4,127,405 11/1978 Levitt .................................. 544/211
4,780,126 10/1988 Diehr et al. ........................ 544/211

FOREIGN PATENT DOCUMENTS 0251079 1/1988 European Pat. Off. .
0304282 2/1989 European Pat. Off. .
3609700 9/1987 Fed. Rep. of Germany .

OTHER PUBLICATIONS

Pfister et al; Chemical Abstract, 1988, 108(17) #150054h.
Conner; Chemical Abstract, 1987, 106 (19) #156500f.

*Primary Examiner*—Mukund J. Shah
*Assistant Examiner*—Y. N. Gupta
*Attorney, Agent, or Firm*—Sprung Horn Kramer & Woods

[57] ABSTRACT

A herbicidal sulphonylurea salt of the formula $$\underset{M^\oplus}{\underset{\ominus}{\text{Ar}-SO_2-N-CO-N}}\overset{R^1}{\underset{}{-}}\underset{X}{\overset{N-Z}{\underset{}{\diagup}}}\underset{R^2}{\overset{Y}{\diagdown}} \quad (I)$$

(with O—R on the aromatic ring)

in which

M$^\oplus$ represents an alkali metal ion or the counterion, formed by protonation, of a basic organic nitrogen compound, R represents halogenoalkyl, R$^1$ represents optionally substituted radicals from the series comprising alkyl, alkenyl, alkinyl or aralkyl, R$^2$ represents hydrogen, halogen, alkyl, halogenoalkyl, alkoxy, halogenoalkoxy, alkylthio, halogenoalkylthio, amino, alkylamino or dialkylamino, X represents nitrogen or a —CH group, Y represents nitrogen or a —CR$^3$ group where R$^3$ represents hydrogen, halogen, cyano, alkyl, formyl, alkyl-carbonyl or alkoxy-carbonyl, and Z represents nitrogen or a —CR$^4$ group where R$^4$ represents hydrogen, halogen, alkyl, halogenoalkyl, alkoxy, halogenoalkoxy, alkylthio, alkylamino or dialkylamino.

7 Claims, No Drawings

PREPARING HERBICIDAL SULPHONYLUREA SALTS

This application is a continuation of application Ser. No. 852,611, filed Mar. 17, 1992, now abandoned, which is a continuation-in-part application of Ser. No. 626,363, filed Dec. 12, 1990, now abandoned.

The invention relates to a new process for preparing sulphonylurea salts, to new sulphonylurea salts and to their use as herbicides.

It is known that sulphonylurea salts are obtained when solutions of sulphonylureas in halogenohydrocarbon solvents are reacted with alkali metal hydroxides or alkaline earth metal hydroxides and the solvent is distilled off, if appropriate, after filtration (cf. EP-A 304,282).

Since in this procedure the product generally does not crystallize from the solution, it is necessary for the solvent to be distilled, which requires large amounts of energy, and the chances of obtaining a purification effect are low.

3-Substituted-1-(2-halogenoalkoxy-benzene-sulphonyl)-3-heteroaryl-(thio)ureas are known as herbicides (cf. EP-A 251,079; U.S. Pat. No. 4,780,126). However, in aqueous medium, these compounds are subject to relatively rapid hydrolytic degradation. It has not yet been possible to prepare salts of these compounds, which should be more stable, of sufficient quality.

A process has now been found for preparing sulphonylurea salts of the general formula (I)

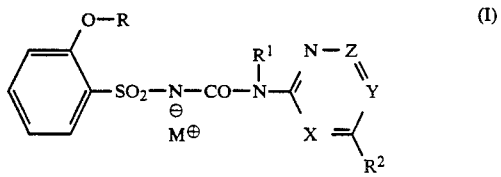

in which

M⊕ represents an alkali metal ion or the counterion, formed by protonation, of a basic organic nitrogen compound, R represents halogenoalkyl, $R^1$ represents optionally substituted radicals from the series comprising alkyl, alkenyl, alkinyl or aralkyl, $R^2$ represents hydrogen, halogen, alkyl, halogenoalkyl, alkoxy, halogenoalkoxy, alkylthio, halogenoalkylthio, amino, alkylamino or dialkylamino, X represents nitrogen or a —CH group, Y represents nitrogen or a —$CR^3$ group where $R^3$ represents hydrogen, halogen, cyano, alkyl, formyl, alkyl-carbonyl or alkoxy-carbonyl, and Z represents nitrogen or a —$CR^4$ group where $R^4$ represents hydrogen, halogen, alkyl, halogenoalkyl, alkoxy, halogenoalkoxy, alkylthio, alkylamino or dialkylamino, which is characterized in that sulphonylureas of the general formula (II)

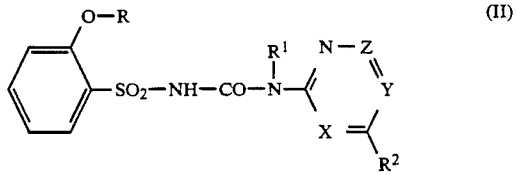

in which R, $R^1$, $R^2$, X, Y and Z have the abovementioned meanings, are reacted with alkali metal hydroxides or with basic organic nitrogen compounds in the presence of hydrocarbons or ethers as diluents at temperatures between 0° C. and 100° C., and the products which are obtained in crystalline form in this process are isolated by customary methods.

Furthermore, it has been found that the sulphonylurea salts of the formula (I) to be prepared by the process according to the invention are distinguished by a powerful herbicidal activity.

The sulphonylurea salts of the formula (I) in which Y represents nitrogen, to be prepared by the process according to the invention, are new and, as new substances, likewise a subject of the present invention.

It is surprising that the sulphonylurea salts of the formula (I) are obtained by the process according to the invention in a very simple manner in very good yields and in high purity, since a smooth reaction of the polar reaction components in hydrocarbons or ethers as non-polar solvents was not to be expected.

As comparison experiments have shown additionally, an analogous reaction in polar solvents results in the formation of a more or less large proportion of degradation products which virtually do not occur in the reaction of the process according to the invention.

Compared with the corresponding "free" sulphonylureas, the new sulphonylurea salts show, in particular, the advantageous property of considerably more stable storage and use forms (formulations and spray liquors).

The process according to the invention preferably relates to preparing sulphonylurea salts and—if Y represents nitrogen—new sulphonylurea salts of the formula (I) in which M⊕ represents a lithium, sodium or potassium ion, a tri-($C_1$–$C_4$-alkyl)-ammonium ion, a N-($C_3$–$C_6$-cycloalkyl)-N,N-di-($C_1$–$C_4$-alkyl)-ammonium ion or in each case the counterion, formed by protonation, of ($C_1$–$C_4$-alkyl)-pyrrolidine, N-($C_1$–$C_4$-alkyl)-piperidine, N-($C_1$–$C_4$-alkyl)-morpholine, N,N'-di-($C_1$–$C_4$-alkyl)-piperazine, N,N-di-($C_1$–$C_4$-alkyl)-benzylamine, 1,5-diazabicyclo-[4.3.0]-non-5-ene (DBN), 1,8-diazabicyclo-[5.4.0]-undec-7-ene (DBU) or 1,4-diazabicyclo-[2.2.2]-octane [DABCO], R represents halogeno-$C_1$–$C_4$-alkyl, $R^1$ represents $C_1$–$C_6$-alkyl (which is optionally substituted by fluorine, cyano, $C_1$–$C_4$-alkoxy or $C_1$–$C_4$-alkylthio), or represents $C_3$–$C_6$-alkenyl and $C_3$–$C_6$-alkynyl (which are optionally substituted by fluorine or chlorine), or represents phenyl-$C_1$–$C_2$-alkyl (which is optionally substituted in the phenyl moiety by fluorine, chlorine, nitro, cyano, methyl, methoxy or $C_1$–$C_2$-alkoxycarbonyl), $R^2$ represents hydrogen, fluorine, chlorine, bromine, methyl, ethyl, trifluoromethyl, methoxy, ethoxy, difluoromethoxy, methylthio, ethylthio, amino, methylamino, ethylamino, dimethylamino or diethylamino, X represents nitrogen or a —CH group, Y represents nitrogen or a —CR³ group where R³ represents hydrogen, fluorine, chlorine, bromine, methyl, formyl, acetyl, methoxycarbonyl or ethoxycarbonyl, and Z represents nitrogen or a —CR⁴ group where R⁴ represents hydrogen, fluorine, chlorine, bromine, methyl, ethyl, trifluoromethyl, methoxy, ethoxy, propoxy, isopropoxy, difluoromethoxy, methylthio, ethylthio, methylamino, ethylamino, dimethylamino or diethylamino.

In particular, the process according to the invention relates to preparing sulphonylurea salts and—if Y represents nitrogen—new sulphonylurea salts of the formula (I)

in which

M⊕ represents a sodium ion or a potassium ion, or represents a trimethyl-, triethyl-, tripropyl- or tributylammonium ion, or a N,N-dimethyl-, N,N-diethyl- or N,N-dipropyl-cyclopentylammonium ion, a N,N-dimethyl-, N,N-diethyl- or N,N-dipropyl-cyclohexylammonium ion, or in each case the counterion, formed by protonation, of N-methyl-, N-ethyl- or N-propyl-pyrrolidine, N-methyl-, N-ethyl- or N-propyl-piperidine, N-methyl-, N-ethyl- or N-propyl-morpholine, N,N'-dimethyl-, N,N'-diethyl- or N,N'-dipropyl-piperazine, N,N-dimethyl-, N,N-diethyl- or N,N-dipropyl-benzylamine, 1,5-diazabicyclo-[4.3.0]-non-5-ene (DBN), 1,8-diazabicyclo-[5.4.0]-undec-7-ene (DBU) or 1,4-diazabicyclo-[2.2.2]-octane. (DABCO), R represents difluoromethyl or trifluoromethyl, R¹ represents methyl, R² represents hydrogen, chlorine, methyl, ethyl, trifluoromethyl, methoxy, ethoxy, difluoromethoxy, methylthio, ethylthio, methylamino, ethylanino or dimethylamino, X represents nitrogen, Y represents nitrogen or a CH group (very particularly preferably nitrogen), and Z represents a C—R⁴ group where R⁴ represents hydrogen, chlorine, methyl, ethyl, trifluoromethyl, methoxy, ethoxy, difluoromethoxy, methylthio, ethylthio, methylamino, ethylamino or dimethylamino.

If, for example, 3-(4,6-dimethoxy-pyrimidin-2-yl)-3-methyl-1-(2-difluoromethoxy-phenylsulphonyl)-urea and trimethylamine are used as starting substances, the course of the reaction in the process according to the invention can be outlined by the following equation:

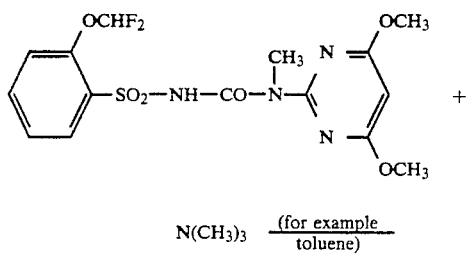

N(CH₃)₃ (for example toluene)

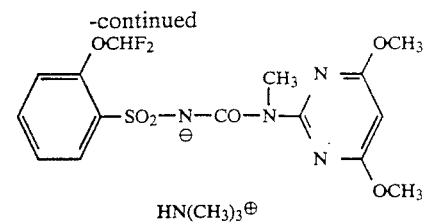

HN(CH₃)₃⊕

Formula (II) provides a general definition of the sulphonylureas to be used as starting substances in the process according to the invention for preparing compounds of the formula (I).

In formula (II), R, R¹, R², X, Y and Z preferably, or in particular, have those meanings which have already been mentioned above in connection with the description of the compounds of the formula (I) according to the invention as being preferred, or particularly preferred, for R, R¹, R², X, Y and Z.

Examples of the starting substances of the formula (II) are listed in Table 1 below.

TABLE 1

Examples of the starting substances of the formula (II)

| R | R¹ | R² | X | Y | Z |
|---|----|----|---|---|---|
| CF₃ | CH₃ | OCH₃ | N | CH | C—OCH₃ |
| CF₃ | CH₃ | CH₃ | N | N | C—OCH₃ |
| CF₃ | CH₃ | OCH₃ | N | CH | C—Cl |
| CF₃ | CH₃ | C₂H₅ | N | CH | C—OCH₃ |
| CF₃ | CH₃ | CH₃ | N | CH | C—OC₂H₅ |
| CF₃ | CH₃ | CH₃ | N | CH | C—OCH₃ |
| CF₃ | CH₃ | CH₃ | N | CH | C—CH₃ |
| CF₃ | CH₃ | CH₃ | N | CH | C—Cl |
| CF₃ | CH₃ | CF₃ | N | CH | C—OCH₃ |
| CHF₂ | CH₃ | OCH₃ | N | CH | C—Cl |
| CHF₂ | CH₃ | OCH₃ | N | CH | C—OCH₃ |
| CHF₂ | CH₃ | CH₃ | N | N | C—CH₃ |
| CHF₂ | CH₃ | CH₃ | N | N | C—OCH₃ |
| CHF₂ | CH₃ | OCH₃ | N | N | C—OCH₃ |
| CHF₂ | CH₃ | CF₃ | N | CH | C—OCH₃ |
| CF₃ | CH₃ | CH₃ | N | N | C—CH₃ |
| CF₃ | CH₃ | C₂H₅ | N | N | C—OCH₃ |
| CF₃ | CH₃ | CH₃ | N | N | C—OC₂H₅ |
| CF₃ | CH₃ | OCH₃ | N | N | C—OCH₃ |
| CF₃ | CH₃ | OC₂H₅ | N | N | C—OC₂H₅ |
| CF₃ | CH₃ | OCH₃ | N | N | C—NHCH₃ |
| CF₃ | CH₃ | OCH₃ | N | N | C—NHC₂H₅ |
| CF₃ | CH₃ | OC₂H₅ | N | N | C—NHCH₃ |
| CF₃ | CH₃ | CH₃ | N | N | C—SCH₃ |
| CF₃ | CH₃ | OCH₃ | N | N | C—SCH₃ |

The starting substances of the formula (II) are known and/or can be prepared by processes known per se (cf. EP-A 251,079).

The process according to the invention is carried out using alkali metal hydroxides or basic organic nitrogen compounds. Preferred substances are lithium hydroxide, sodium hydroxide and potassium hydroxide, tri-(C₁–C₄-alkyl)-amine, N- (C₃–C₆-cycloalkyl)-N,N-di-(C₁–C₄-alkyl)-amine, N-(C₁–C₄-alkyl)-pyrrolidine, N-(C₁–C₄-alkyl)-piperidine, N-(C₁–C₄-alkyl)-morpholine, N,N'-di-(C₁–C₄-alkyl)piperazine, N,N-di-(C₁–C₄-alkyl)-benzylamine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO).

Particularly preferred substances are sodium hydroxide and potassium hydroxide, trimethyl-, triethyl-, tripropyl- and tributylamine, N,N-dimethyl-,N,N-diethyl- and N,N-dipropyl-cyclopentylamine, N,N-dimethyl-, N,N-diethyl- and N,N-dipropyl-cyclohexylamine, N-methyl-, N-ethyl- and N-propyl-pyrrolidine, N-methyl-, N-ethyl- and N-propyl-piperidine, N-methyl-, N-ethyl- and N-propyl-morpholine, N,N'-dimethyl-, N,N'-diethyl- and N,N'-dipropyl-piperazine, N,N-dimethyl-, N,N-diethyl- and N,N-dipropyl-benzylamine, 1,5-diazabicyclo-[4.3.0]-non-5-ene (DBN), 1,8-diazabicyclo-[5.4.0]-undec-7-ene (DBU) and 1,4-diazabicyclo-[2.2.2]-octane (DABCO).

The process according to the invention is carried out in the presence of hydrocarbons or ethers as diluents. Diluents which are preferred in the process according to the invention are aromatic, in particular benzoidal hydrocarbons, which contain, if appropriate, 1 to 3 alkyl substituents, each of which has 1 to 3 carbon atoms, or are dialkyl ethers which contain one alkyl group having 1 to 4 carbon atoms (where the groups having 3 or 4 carbon atoms can be straight or branched) and one further alkyl group being α-branched and having 3 or 4 carbon atoms.- Examples of these which may be mentioned are: benzene, toluene, o-, m- and p-xylene, ethylbenzene, propylbenzene, cumene, 1,2,3-trimethylbenzene, 1,2,4-trimethylbenzene, 1,3,5-trimethylbenzene, di-isopropylether, di-sec.-butyl ether and tert.-butyl methyl ether. Toluene and tert.-butyl methyl ether are very particularly preferred as diluents in the process according to the invention.

In the process according to the invention, the reaction temperatures can be varied within a substantial range. In general, the process is carried out at temperatures between 0° C. and 100° C., preferably at temperatures between 10° C. and 50° C.

In general, the process according to the invention is carried out under atmospheric pressure. However, it is also possible to carry out the process under increased or reduced pressure.

For carrying out the process according to the invention, between 0.9 and 1.5 moles, preferably between 1.0 and 1.3 moles, of an alkali metal hydroxide or a basic organic nitrogen compound are generally employed per mole of sulphonylurea of the formula (I).

The reactants can be combined in any desired sequence. In a preferred embodiment of the process according to the invention, the sulphonylurea of the formula (I) is first stirred with the hydrocarbon diluent, and an alkali metal hydroxide or a basic organic nitrogen compound is then added. The reaction mixture is stirred until crystallization of the product is virtually complete; the product is subsequently isolated by filtration with suction.

The active compounds of the formula (I) can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop-fields, on lawn, turf and pasture-land, and for the selective combating of weeds in annual cultures.

The compounds of the formula (I) according to the invention are particularly suitable for selectively combating dicotyledon weeds in monocotyledon cultures as a pre-emergence or post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); N-(methoxymethyl)-2,6-diethyl-chloroacetanilide (ALACHLOR); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); 2-[4-(2,4-dichlorophenoxy)-phenoxy]-propanoic acid, its methyl ester or its ethyl ester (DICLOFOP); S-ethyl N,N-di-n-propylthiocarbamate (EPTAME); 4-amino-6-t-butyl-3-ethylthio-1,2,4-triazin-5(4H)-one (ETHIOZINE); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy)-propanoic acid or its butyl ester (FLUAZIFOP); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or its 1-methylheptyl ester (FLUROXYPYR); 2-{4-[(3-chloro-5-(trifluoromethyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (REXAZINONE); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl)-acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); (2-chloro-4-trifluoromethylphenyl)-(3-ethoxy-4-nitro-phenyl) ether (OXYFLUORFEN); N-(1-ethyl-propyl)-3,4-dimethyl-2,6-dinitroaniline (PENDIMETHALIN); 2-chloro-N-isopropylacetanilide (PROPACHLOR); O-(6-chloro-3-phenyl-pyridazin-4-yl) S-octyl thiocarbamate (PYRIDATE); ethyl 2-[4-(6-chloro-quinoxalin-2-yl-oxy)-phenoxy]-propionate (QUIZALOFOP-ETHYL); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE methyl 3-[[[[(4-methoxy-6-methyl-1,3,5-triazin-2-yl)-amino]-carbonyl]-amino]-sulphonyl]-thiophene-2-carboxylate (THIAMETURON); S-(2,3,3-trichloro-allyl) N,N-diisopropylthiocarbamate (TRI-ALLATE) and 2,6-dinitro-4-trifluoromethyl-N,N-dipropylaniline (TRIFLURALIN). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 1000 g of active compound per hectare of soil surface, preferably between 5 g and 500 g per ha.

The preparation and use of the active compounds according to the invention can be seen from the following examples.

PREPARATION EXAMPLES

Example 1

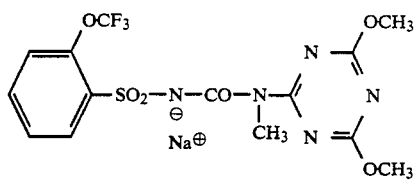

4.4 g (0.010 mol) of 3-(4,6-dimethoxy-s-triazin-2-yl)-3-methyl-1-(2-trifluoromethoxy-phenylsulphonyl)-urea are stirred with 15 ml of toluene, and 0.5 g (0.0125 mol) of sodium hydroxide powder are then added. The reaction mixture is stirred for 60 minutes at 20° C. to 25° C., which results in the formation of a viscous crystalline paste which is kept stirrable by adding a total of 30 ml of toluene. When the reaction is complete, the crystalline product is isolated by filtration with suction.

4.0 g (87% of theory) of the sodium salt of 3-(4,6-dimethoxy-s-triazin-2-yl)-3-methyl-1-(2-trifluoromethoxy-phenylsulphonyl)-urea are obtained; melting point 224° C.

Example 2

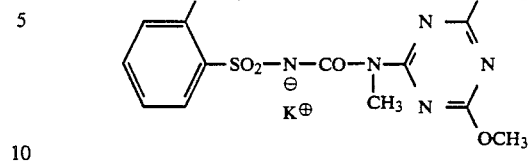

4.4 g (0.010 mol) of 3-(4,6-dimethoxy-s-triazin-2-yl)-3-methyl-1-(2-trifluoromethoxy-phenylsulphonyl)-urea are stirred with 50 ml of toluene, and 0.8 g of 80% potassium hydroxide powder (0.0114 mol of KOH) is then added. The reaction mixture is stirred for 15 hours at 20° C. to 25° C., and the product which is obtained as crystals is isolated by filtration with suction.

4.1 g (86% of theory) of the potassium salt of 3-(4,6-dimethoxy-s-triazin-2-yl)-3-methyl-1-(2-trifluoromethoxy-phenylsulphonyl)-urea are obtained; melting point 193° C. (decomposition).

Other examples which can be prepared analogously are the compounds of the formula (I) listed in Table 2 below.

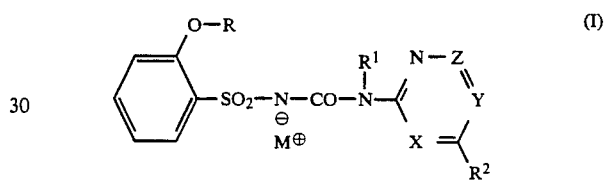

TABLE 2

Examples of the compounds of the formula (I)

| Example No. | R | $R^1$ | $R^2$ | X | Y | Z | $M^{\oplus}$ | Melting point (°C.) |
|---|---|---|---|---|---|---|---|---|
| 3 | $CF_3$ | $CH_3$ | $CH_3$ | N | N | $C-CH_3$ | $Na^{\oplus}$ | 98 |
| 4 | $CF_3$ | $CH_3$ | $CH_3$ | N | N | $C-OCH_3$ | $Na^{\oplus}$ | >240 (decomp.) |
| 5 | $CF_3$ | $CH_3$ | $OCH_3$ | N | N | $C-OCH_3$ | $(C_2H_5)_3NH^{\oplus}$ | 125 (decomp.) |
| 6 | $CHF_2$ | $CH_3$ | $CH_3$ | N | N | $C-OCH_3$ | $Na^{\oplus}$ | 250 |
| 7 | $CHF_2$ | $CH_3$ | $OCH_3$ | N | N | $C-OCH_3$ | $Na^{\oplus}$ | 205 |
| 8 | $CF_3$ | $CH_3$ | $OCH_3$ | N | N | $C-OCH_3$ | $(CH_3)_3NH^{\oplus}$ | 119 |
| 9 | $CF_3$ | $CH_3$ | $OCH_3$ | N | N | $C-OCH_3$ | cyclohexyl-$NH(CH_3)_2^{\oplus}$ | 82 |
| 10 | $CF_3$ | $CH_3$ | $OCH_3$ | N | N | $C-OCH_3$ | pyrrolidinyl-$NHCH_3^{\oplus}$ | 114 |
| 11 | $CF_3$ | $CH_3$ | $OCH_3$ | N | N | $C-OCH_3$ | piperazinyl-$NH^{\oplus}$ | 121 |
| 12 | $CF_3$ | $CH_3$ | $OCH_3$ | N | N | $C-OCH_3$ | $H^{\oplus}$ on bicyclic amidine | 108 |
| 13 | $CF_3$ | $CH_3$ | $CH_3$ | N | N | $C-OCH_3$ | $K^{\oplus}$ | 200 |

TABLE 2-continued

Examples of the compounds of the formula (I)

| Example No. | R | R¹ | R² | X | Y | Z | M⊕ | Melting point (°C.) |
|---|---|---|---|---|---|---|---|---|
| 14 | CF$_3$ | CH$_3$ | CH$_3$ | N | N | C—OCH$_3$ | 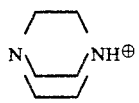 | 135 |

Example 1a

The compound described in Example 1 can also be prepared as follows, for example:

18.0 g (0.041 mol) of 3-(4,6-dimethoxy-s-triazin-2-yl)-3-methyl-1-(2-trifluoromethoxy-phenylsulphonyl)-urea are stirred with 150 ml of tert.-butyl methyl ether, and 1.7 g (0.041 mol) of sodium hydroxide(micro pills) are then added. The reaction mixture is stirred for 30 hours at 20° C., and the product which is obtained as crystals is isolated by filtration with suction.

18.8 g of the sodium salt of 3-(4,6-dimethoxy-s-triazin-2-yl)-3-methyl-1-(2-trifluoromethoxy-phenylsulphonyl)-urea (content: 96.3%, yield: 97.1%) are obtained.

For example, the compound given in Table 2 as Example 5 can be prepared as follows:

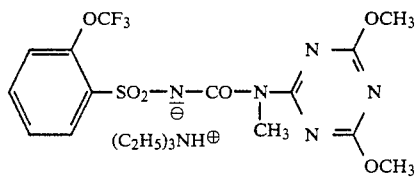

8.8 g (0.02 mol) of 3-(4,6-dimethoxy-s-triazin-2-yl-3-methyl-1-(2-trifluoromethoxy-phenylsulphonyl)-urea are dissolved in 88 ml of toluene by heating to approximately 40° C.; 2.2 g (0.021 mol) of triethylalmine are subsequently added at 35° C. to 40° C. The product starts to crystallize after a few minutes. The mixture is stirred for another approximately 15 hours at 20° C., and the crystalline product is then isolated by filtration with suction.

8.8 g (82% of theory) of the triethylammonium salt of 3-(4,6-dimethoxy-s-triazin-2-yl)-3-methyl-1-(2-trifluoromethoxy-phenylsulphonyl)-urea are obtained; melting point: 125° C. (decomposition).

Comparative Trials using different solvents:

When the reaction of Example I was repeated, but using different (conventional) solvents, very unsatisfactory results were obtained.

The solvents used and the yields of the sodium salt obtained are shown in the following Table 3.

TABLE 3

| Solvent used in process of Example 1 | Yield of compound of Example 1 |
|---|---|
| acetone | 21% of theory |
| methyl isobutyl ketone | 31% of theory |
| methylene chloride | 64.5% of theory |
| dipropylene glycol | (traces only) |

In none of these trials was the balance (to 100% yield theoretically) still unreacted starting material, but rather was degradation product formed by hydrolysis.

Formulation Examples (a) Formulation I—according to the invention

To produce a suitable wettable powder (WP-formulation) of the compound of Example 1, the following components were mixed intensely (using a Loedige mixer), then finely ground (using an air-jet mill) and thereafter mixed again until homogeneity was achieved (average particles size: 3–8 µm):

85.1% of the sodium salt of 3-(4,6-dimethoxy-s-triazin-2-yl)-3-methyl-1-(2-trifluoromethoxy-phenylsulphonyl)-urea (see Example 1—corresponding to 81.0% of the "free" sulphonylurea), 0.5 of an alkylnaphthylsulphonate as wetting agent, 2.0% of an alkylarylsulphonate-formaldehyde-co-condensate (molecular weight of about 800 Dalton) as dispersing agent, 5.0% of a highly-dispersed silica, balance: an inorganic filler (clay).

(b) Formulation II—according to the prior art

In the same way as in case of Formulation I a wettable powder (WP-formulation) of the corresponding "free" sulphonylurea was produced, containing the following components:

70.0% of 3-(4,6-dimethoxy-s-triazin-2-yl)-3-methyl-1-(2-trifluoromethoxy-phenylsulphonyl)-urea (i.e. the starting material used in Example 1), 1.0% of an alkylnaphthylsulphonate as wetting agent, 5.0% of an alkylarylsulphonate-formaldehyde-co-condensate (molecular weight of about 800 D.), 7.0% of a highly-dispersed silica, 5.0% of NAHCO$_3$, balance: an inorganic filler (clay).

(c) Comparative Stability Test:

Samples of the above WP Formulations I and II were filled into glass bottles in equal amounts and stored in a thermostatic box at various temperatures and for various periods of time.

A typical storage experiment showed the following stability results, obtained by analysis of the concentration of still-existing active ingredient (a.i.), determined in percent (%) of the "free" (organic) sulphonylurea, based on the weight of the entire formulation:

| Formulation I - according to the invention (WP, 81% a.i.) | | |
|---|---|---|
| | Time | |
| Temperature | after 2 weeks | after 8 weeks |
| at −10° C. | 80.9% | |
| at +20° C. | | 81.0% |
| at +40° C. | | 79.3% |
| at +54° C. | 81.4% | 77.7% |

This experiment proves the high chemical stability of the sodium salt disclosed in Example 1, as desired.

After 2 weeks at +54° C., there is observed no loss of a.i. Even after 8 weeks at 54° C., a loss of only 3.3% (from 81.0% to 77.7%) was observed.

This minimal loss of 3.3% (absolute) under the given conditions corresponds to a loss of 4.1%, relative to the original content of 81.0%.

| Formulation II - according to the invention (WP, 70% a.i.) | | |
|---|---|---|
| | Time | |
| Temperature | after 2 weeks | after 8 weeks |
| at −10° C. | | |
| at +20° C. | 69.7% | 69.3% |
| at +40° C. | | 59.2% |
| at +54° C. | 54.5% | 41.1% |

This experiment shows the lack of stability of the "free" sulphonylurea upon storage.

After 2 weeks at +54° C., there is observed a loss of 15.5% (from 70.0% to 54.5%) of a.i. After 8 weeks at +54° C., a loss of 28.9% (from 70.0% to 41.1%) was determined.

This actual loss of 28.9% (absolute) under the given test conditions corresponds to a loss of 41.3%, relative to the original content of 70.0%.

USE EXAMPLES

Example A

Post-emergence test

Solvent: 5 parts by weight of dimethylformalmide

Emulsifier: 1 part by weight of alkylaryl polyglycol ether

Additive: 0.1% Renex-36 (=polyoxyethylene(6) tridecyl ether; wetting agent)

To produce a suitable preparation of active compound, 1 part by weight of active compound is mixed with the stated amount of solvent, the stated amount of emulsifier and additive is added and the concentrate is diluted with water to the desired concentration.

Test plants which have a height of 5-15 cm are sprayed with the preparation of active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, for example, the compounds of Preparation Examples 1, 2, 4, 5, 8, 9, 10, 11 and 12 have a very powerful action against weeds combined with a very good tolerance by wheat, barley and corn.

Example B

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds of Preparation Examples 1, 2, 4 and 5 have a very powerful action against weeds combined with a very good tolerance by wheat, barley and corn.

It is understood that the specification and examples are illustrative but not limitative of the present invention and that other embodiments within the spirit and scope of the invention will suggest themselves to those skilled in the art.

We claim:

1. A sulphonylurea salt of the formula

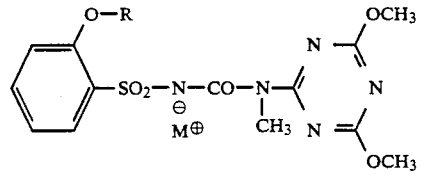

in which

R is $CF_3$ or $CHF_2$, and $M^\oplus$ is $Na^\oplus$ or $K^\oplus$.

2. A sulphonylurea salt according to claim 1, in which R is $CF_3$.

3. A sulphonylurea salt according to claim 1, in which R is $CHF_2$.

4. A sulphonylurea salt according to claim 2, in which $M^\oplus$ is $Na^\oplus$.

5. A sulphonylurea salt according to claim 3, in which $M^\oplus$ is $Na^\oplus$.

6. A herbicidal composition comprising a herbicidally effective amount of a salt according to claim 1 and a diluent.

7. A method of combating undesired vegetation which comprises applying to such vegetation or to a locus from which it is desired to exclude such vegetation a herbicidally effective amount of a salt according to claim 1.

* * * * *